(12) United States Patent
Ramsauer

(10) Patent No.: US 7,835,490 B2
(45) Date of Patent: Nov. 16, 2010

(54) MAMMOGRAPHY APPLIANCE

(75) Inventor: Martin Ramsauer, Pyrbaum (DE)

(73) Assignee: Siemens Aktiengesellschaft, Munich (DE)

( * ) Notice: Subject to any disclaimer, the term of this patent is extended or adjusted under 35 U.S.C. 154(b) by 55 days.

(21) Appl. No.: 12/162,263

(22) PCT Filed: Jan. 5, 2007

(86) PCT No.: PCT/EP2007/050118

§ 371 (c)(1),
(2), (4) Date: Dec. 3, 2008

(87) PCT Pub. No.: WO2007/088089

PCT Pub. Date: Aug. 9, 2007

(65) Prior Publication Data

US 2009/0304146 A1    Dec. 10, 2009

(30) Foreign Application Priority Data

Feb. 1, 2006    (DE) .................. 10 2006 004 590

(51) Int. Cl.
*A61B 6/04* (2006.01)
(52) U.S. Cl. ......................................... 378/37; 378/197
(58) Field of Classification Search .................. 378/37, 378/193, 196, 197, 198
See application file for complete search history.

(56) References Cited

U.S. PATENT DOCUMENTS

| | | | |
|---|---|---|---|
| 3,281,598 A * | 10/1966 | Hollstein | 378/179 |
| 5,305,365 A | 4/1994 | Coe | |
| 7,103,140 B2 * | 9/2006 | Amitani et al. | 378/37 |
| 7,308,295 B2 * | 12/2007 | Ihamaki et al. | 600/407 |
| 2005/0054915 A1 | 3/2005 | Sukovic et al. | |
| 2005/0100129 A1 | 5/2005 | McKenna | |
| 2007/0274438 A1 * | 11/2007 | Hyvarinen et al. | 378/37 |

FOREIGN PATENT DOCUMENTS

| | | |
|---|---|---|
| DE | 26 40 248 A1 | 3/1978 |
| DE | 197 28 023 A1 | 1/1998 |
| DE | 103 53 611 A1 | 6/2005 |
| WO | WO 94/06352 A1 | 3/1994 |

OTHER PUBLICATIONS

German Office Action dated Nov. 14, 2006 with English translation.
Written Opinion dated Jun. 6, 2007 with English translation.

* cited by examiner

*Primary Examiner*—Hoon Song
(74) *Attorney, Agent, or Firm*—Brinks Hofer Gilson & Lione

(57) ABSTRACT

To permit a compact and structurally simple design of a mammography appliance, an irradiation unit is secured on a C-arm, which lies in a swivel plane that is perpendicular to a horizontal axis. In this way, only slight mechanical leverages act on the support arm. At the same time, the C-arm design creates a free space, which is used in particular also for the arrangement of a display and/or control panel and for the arrangement of a biopsy unit.

18 Claims, 4 Drawing Sheets

MAMMOGRAPHY APPLIANCE

The present patent document is a nationalization of PCT Application Ser. No. PCT/EP2007/050118, filed Jan. 5, 2007, designating the United States, which is hereby incorporated by reference. This application also claims the benefit of DE 10 2006 004 590.4, filed Feb. 1, 2006, which is hereby incorporated by reference.

BACKGROUND

The present embodiments relate to a mammography appliance with a stand, to which an appliance rack is attached. The mammography appliance includes a compressing unit with an object table and a compressing plate.

A mammography appliance is used to perform medical examinations of the soft tissue of the human breast with X-ray radiation. The medical examinations are used for the early identification of breast cancer. The breast is clamped between the object table and the compression plate, which can be moved toward the object table. An X-ray examination is then performed with the irradiation unit embodied as an X-ray tube. An X-ray detector is integrated in the object table. During the irradiation, soft X-ray radiation in the range below 50 kV, in particular below 30 kV is used.

Mammography appliances, such as the "Mammomat 1000", "Mammomat 3000 Nova" and "Mammomat Novation," have a similar structural design. As a representative example, the "Mammomat Novation" has a main body embodied as a stand and an appliance arm protruding from the stand at an angle at the free end of which a radiation source is arranged. The appliance arm is implemented as a sheet-metal structure and connected in a rotationally fixed manner to a horizontal rotary axis of the mammography appliance so that the radiation source can be swiveled 360° about an isocenter. An object table is mounted on the appliance arm by a rotary joint and can be swiveled 360° about the isocenter.

The protruding angled appliance arm, to which the irradiation unit and the compression unit are attached, exerts high mechanical leverage forces, which require a complex mechanical design. The appliance arm also performs the rotary or swivel movements required for the different types of examination. For example, the mammography device is usually used for screening examinations, in which the irradiation unit is located in a 0° position. The irradiation unit and the object table are arranged opposite each other in the longitudinal direction. The mammography appliance is designed for a stereotactic examination in which the breast is irradiated from two different angles. The irradiation unit is swiveled out of the resting position by ±10° or by ±15° about the horizontal axis with a fixed object table. Tomosynthesis examinations may be performed with the mammography appliance in which the irradiation unit moves continuously over a comparatively large angular range, for example, in an angular range of ±25° about the horizontal axis with a fixed object table. It is usually possible to produce an MLO (mediolateral oblique) view. During this kind of examination, the irradiation unit again moves over a large angular range, wherein the object table follows the irradiation unit so that the object table and irradiation unit are always aligned in the same position respective to each other and at the same distance from each other. The mammography appliance permits imaging of the breast to be examined in standard views, such as craniocaudal (CC) or mediolateral oblique (MLO) views.

SUMMARY AND DESCRIPTION

The present embodiments obviate one or more of the problems or drawbacks inherent in the related art. For example, in one embodiment, a mammography device has a simple design.

In one embodiment, a mammography appliance includes an irradiation unit that is attached to a C-arm-type support arm, lying in a swivel plane perpendicular to a horizontal axis. Within the swivel plane, the irradiation unit can be swiveled in the case of, for example, a stereotactic or tomosynthesis examination.

A C-arm-type support arm is a support arm bent in a C shape. The C-arm is arranged within the swivel plane and does not extend in the direction of the horizontal axis. Compared to the conventional, bent appliance arm, lower leverage forces are exerted on the stand. The C-arm design of the support arm defines a circular path on which the irradiation unit travels during a swivel movement. The use of the C-arm-type support arm also, alternately, overrides or, at least alternately, attenuates the active leverages so that the leverages acting on the stand are low. The C-arm achieves a very stable and simultaneously very compact design. The C-arm between the irradiation unit and the object table creates a free space with no supporting elements which is now available for other functional assemblies.

To enable the irradiation unit to swivel, the support arm itself is swivel-mounted. Alternatively, or supplementarily, the support arm is telescopic and the irradiation unit is arranged on a movable telescopic arm. The support arm may be arranged in an immobile and fixed manner and the telescopic arm to be extended or retracted to facilitate the swivel movement of the irradiation unit. Since the support arm overall has a C-arm design, the telescopic arm is bent in accordance with the bend in the C-arm. On the extension of the telescopic arm, the irradiation unit is moved along a circular line.

In one embodiment, the telescopically-designed support arm and the swivel mounting of the support arm are combined. The two swivel mechanisms may be matched to each other in such a way that the telescopic swivel movement can be used, for example, to perform the swivel movement of ±10° or ±15° usually required for a stereotactic examination or that of ±25° for a tomosynthesis examination. If a more extensive rotary movement is desired for the MLO examination, the support arm overall is swiveled, together with the object table. The swivel movement of the support arm is directly coupled to the swivel movement of the object table, so that there is a rigid connection between the support arm and the object. When the telescopic arm is extended, the object table remains in its usually horizontal initial position.

In an alternative embodiment, a swivel movement of the whole support arm is provided during the stereotactic and/or tomosynthesis examination. The object table is decoupled or decouplable from the swivel movement of the support arm so that the object table remains in its normal horizontal position. The object table can be coupled to the swivel movement of the support arm for an MLO examination.

The support arm in the swivel plane is arranged directly in front of the stand, or alternatively, above or below the stand. Accordingly, the leverage forces acting on the stand are kept as low as possible. In one embodiment, the C-arm is arranged parallel to the front side of the stand directly adjacent to this front side. "Arranged . . . directly" means at the most a distance of a few centimeters. In another embodiment, the support arm is arranged on the face end of the stand when viewed in the longitudinal direction of the stand. With this face-end arrangement, the stand and the support arm are preferably arranged in alignment with each other in the longitudinal direction so that no leverage forces act on the stand. With the arrangement above the stand, the stand is attached at the base and with the arrangement below the stand it is attached to a ceiling. The base-side arrangement of the stand has a high mechanical stability, since here the weight forces of both the stand and the support arm are transmitted along the longitudinal direction into the base.

In one embodiment, the stand includes a bearing element to which the support arm is attached. In the embodiment with the support arm attached in a swivelable manner to the stand the support arm is rotatably mounted about the horizontal axis on the bearing element. In the embodiment with a face-end arrangement of the support arm on the stand, the support arm is attached to the stand by the bearing element.

The support arm is mounted on the bearing element with an end-side mounting end. The irradiation unit is arranged at the other end of the support arm. The irradiation unit and mounting point are arranged opposite each other on the two ends of the C-arm. Alternatively to this, the support arm is guided in the support element in the style of a sliding bearing so that the support arm is guided along the bearing element. A swivel movement of the support arm varies the angular distance between the mounting point (bearing element) and the irradiation unit.

In one embodiment, the compression unit is attached rotatably on the bearing element and about the horizontal axis. The support arm and compression unit are attached together on the bearing element. The compression unit is rigidly connected to the support arm. Alternatively, the compression unit is decoupled and attached rotatably on the bearing element independently of the support arm.

In one embodiment, the appliance rack includes a biopsy unit which can be moved from a parked position into a biopsy position. During a biopsy, a tissue sample is taken, usually by a needle. The parked position is arranged in a free parking space encompassed by the C-arm-type support arm. The free space created by the use of the C-arm is used for this parked position. The parking space lies within the swivel plane. Using the C-arm, even on the swiveling of the support arm or the irradiation unit, there is no risk of collision with the biopsy unit.

The biopsy unit is swivel-mounted on the compression unit. The biopsy unit is moved into the biopsy position without problems. This permits a particularly compact and simple structural design.

The free space created by the C-arm is expediently utilized in such a way that a display and/or operator panel is arranged on the stand and to be precise in such a way that the operating personnel can view or access this from the front without, for example, a component of the appliance, such as the irradiation unit or the compression unit obstructing the access to or the view of display and/or operator panel.

In order to be able to set a vertical adjustment and hence an adaptation to the height of a person to be examined, the stand may be vertically adjustable together with the appliance rack, for example, when the appliance rack is firmly connected to the stand with respect to vertical adjustability. Alternatively, the appliance rack is vertically adjustable relative to the stand, for example, when the stand itself is not vertically adjustable. The two mechanisms for height adjustment can also be combined with each other.

DETAILED DESCRIPTION

Figure 1C:
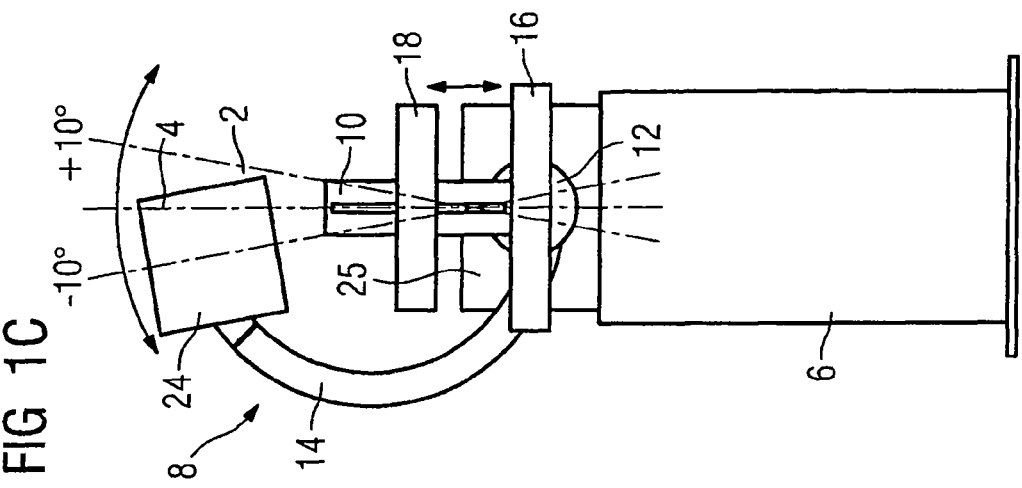
FIG. 1A-1C illustrate a front view of a mammography appliance in different irradiation situations.
Figure 1B:
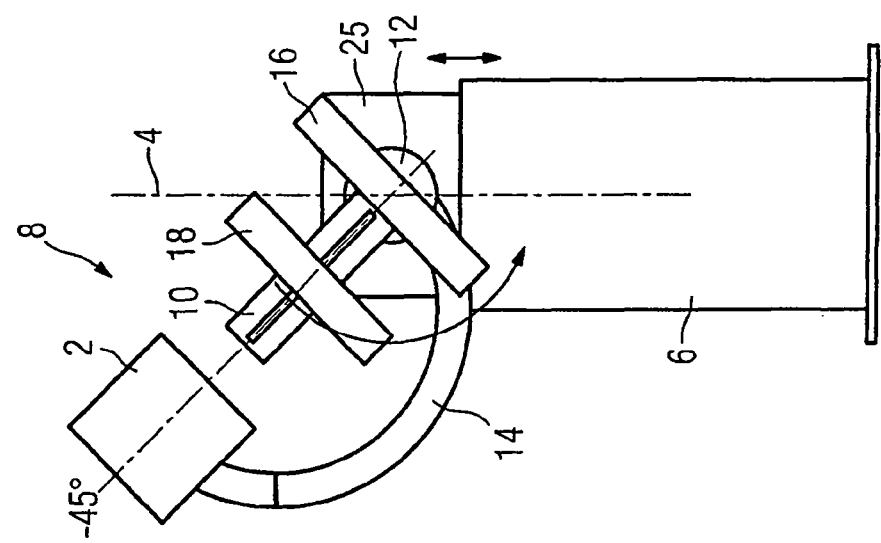
Figure 1A:
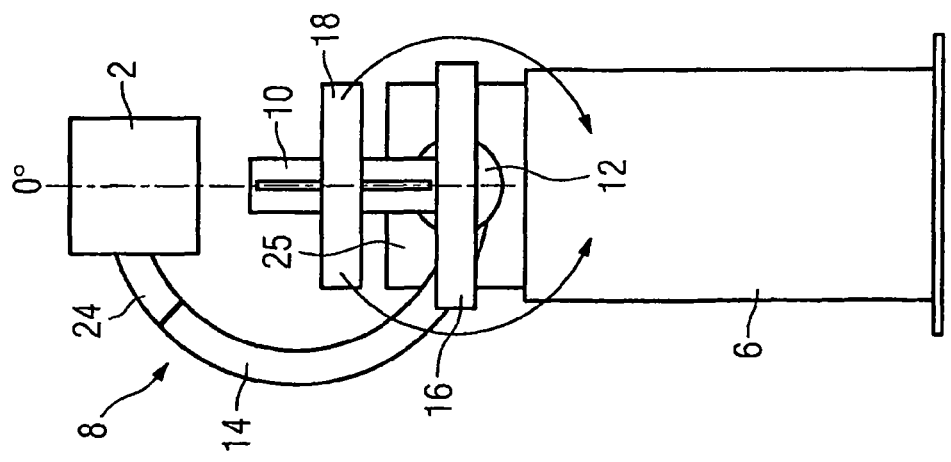

FIG. 1A, 1B, 1C show a front view of a mammography appliance in the typical irradiation and examination situations for a mammography. FIG. 1A shows the mammography appliance in a 0° position for a screening examination (CC image: craniocaudal). In this 0° position, an irradiation unit 2 is located in a 12-o'clock position and is oriented parallel to a vertical longitudinal direction 4. FIG. 1B shows the mammography appliance in a 45° position for an MLO image (mediolateral oblique). In the view according to FIG. 1B, the irradiation unit 2 is deflected by 45° relative to the longitudinal direction 4. FIG. 1C shows the irradiation situation for a stereotactic examination performed concomitantly with a biopsy. During this stereotactic examination, the irradiation unit is usually swiveled ±10° or ±15° relative to the longitudinal direction 4. The position shown in FIG. 1A is also described as the craniocaudal (CC) position, and the position shown in FIG. 1B is also described as the mediolateral oblique (MLO) position.

The different variants of the mammography appliance described here are usually embodied in such a way that they can be used for all irradiation variants. A modular design of the mammography appliance is provided so that alternatively in each case only certain irradiation situations are possible. With a pure screening system, for example, there is no separate swivelability and the irradiation unit is fixed relative to the object table. With a stereotactic system, the swiveling movement of the irradiation unit 2 is restricted, for example, by a stop, to a swivel movement of ±10° or ±15°. With a system, which is also provided for tomosynthesis, continuous movement is provided over a large angular range. The concepts described in the following for the design of the mammography appliance relate to a modular design with which optionally the respective mammography appliances for the different applications can be specified.

Figure 3:
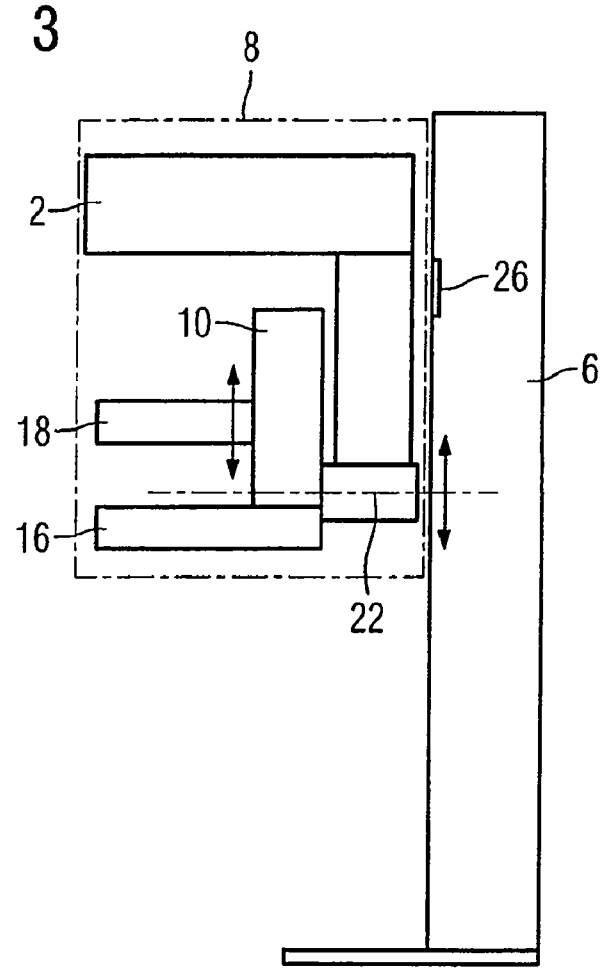
FIG. 3 illustrates a top view of an alternative embodiment of a mammography appliance.

The mammography appliance includes a stand 6, to which is attached an appliance rack 8 (see dashed line in FIG. 3). The appliance rack 8 has the irradiation unit 2, a compression unit 10, a bearing element 12 and a C-arm support arm 14, which is also referred to as a C-arm for short. Arranged on the bearing element 12, are an object table 16 and the compression unit 10. The compression unit 10 includes a compression plate 18, which is arranged displaceably relative to the object table 16. A type of rail guide is provided in the compression unit 10.

Figure 2:
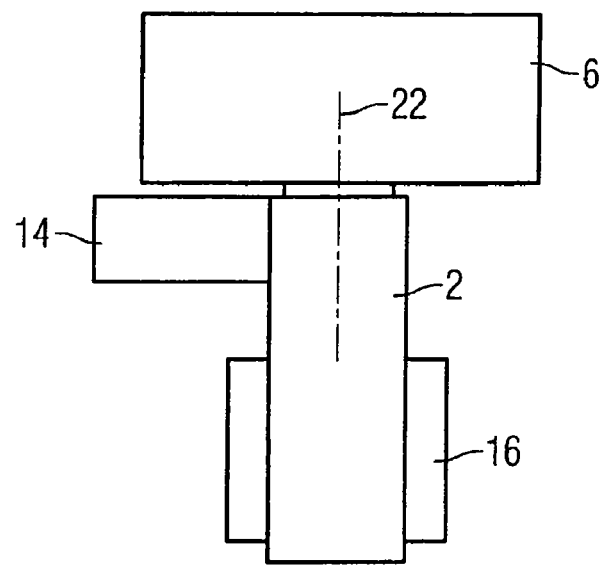
FIG. 2 illustrates a top view of a mammography appliance.

One end of the C-arm 14 is attached to the bearing element 12 so that the mounting end of the C-arm formed is attached and the C-arm can rotate about a horizontal axis 22 (see in particular FIGS. 2, 3). At its other end, the C-arm bears the irradiation unit 2. The irradiation unit 2 includes an X-ray tube and a diaphragm, wherein the X-ray tube emits soft X-ray radiation when in operation.

The C-arm 14 is a telescopic arm and has an extendable telescopic arm 24 on the end-side of which the irradiation unit 2 is arranged. The retraction and extension of the telescopic arm 24 causes a swivel movement of irradiation unit 2 to take place. The swivel movement facilitated by the telescopic arm 24 takes place in a swivel region required for the stereotactic examination. For a stereotactic examination, it is sufficient to retract or extend the telescopic arm. The C-arm 14 itself is not swiveled. The telescopic system establishes predefined stop positions for the irradiation unit 2, which it then adopts alternately in each case. (FIG. 1C). Similarly, with a tomosynthesis examination, it is only necessary to move the telescopic arm 24 in order to swivel the irradiation unit 2 by ±25°.

If an MLO examination is desired, the entire C-arm 14 is swiveled about the horizontal axis 22 without the telescopic arm being moved (see FIG. 1B).

The compression unit 10 is connected to the bearing element 12, whereby here preferably joint rotatability with the C-arm 14 is facilitated so that the irradiation unit 2 is always aligned in the same orientation to the object table 16 (FIG. 1B). The bearing element 12 is formed by a bearing shaft connected to the stand, which is encompassed in a sleeve-like way by a rotatable bearing shell. The bearing shell forms the mounting end of the C-arm 14. Simultaneously, the compression unit 10 is firmly mechanically connected to this bearing shell so that no relative motion is enabled between the mounting end of the C-arm 14 and the compression unit 10.

Alternatively, the compression unit 10 is rotatably mounted about the horizontal axis 22 independently of the C-arm 14. It is possible to dispense with the telescopic embodiment of the C-arm 14 and to swivel the C-arm 14 during a stereotactic examination and simultaneously leave the compression unit 10 in the horizontal alignment as is usual during a stereotactic examination.

As shown in FIG. 1A-1C, the stand 6 includes a lifting or telescopic device so that vertical adjustment is possible. The bearing element 12 is attached to an extensible lifting element 25. The appliance rack 8 is substantially arranged above the stand 6 or substantially abuts the stand 6 commencing with the bearing element 12.

In an alternative embodiment, as shown in FIG. 3, the stand 6 is not vertically adjustable. Instead, the appliance rack 8 is vertically adjustable relative to the stand 6, as indicated by a double arrow. The bearing element 12 is displaceable in the longitudinal direction 4.

The support arm, as a C-arm 14, lies within a swivel plane perpendicular to the horizontal axis 22. The C-arm 14 clamps a plane perpendicular to the horizontal axis 22. The support arm 14 does not protrude or only protrudes slightly forward from the stand 6 so that here only low leverage forces are exerted on the stand. The embodiment of the C-arm 14 achieves a structurally very stable design, which also facilitates the necessary swivel movements.

A further decisive advantage of the C-arm-type embodiment can be seen in that created between the two ends of the C-arm is a free space in which no support elements are arranged. The free space is utilized in the sense of a high degree of user friendliness to the effect that arranged on the stand 6 there is a display and/or operator panel 26, which is visible to the operating personnel from the front, and independently of the respective rotary position of the irradiation unit 2. As shown in FIG. 3, the display field 26 is hereby arranged above the compression unit 10 and below the irradiation unit 2 on the center of the stand 6.

As can be seen in particular in the side view in FIG. 3, the C-arm 14 is placed directly in front of the front side of the stand 6 and between the stand 6 and the compression unit 10. The design forms an interspace between the compression unit 10 and the stand 6, which is used as a parking space 28 for a biopsy unit 30.

Figure 4A:
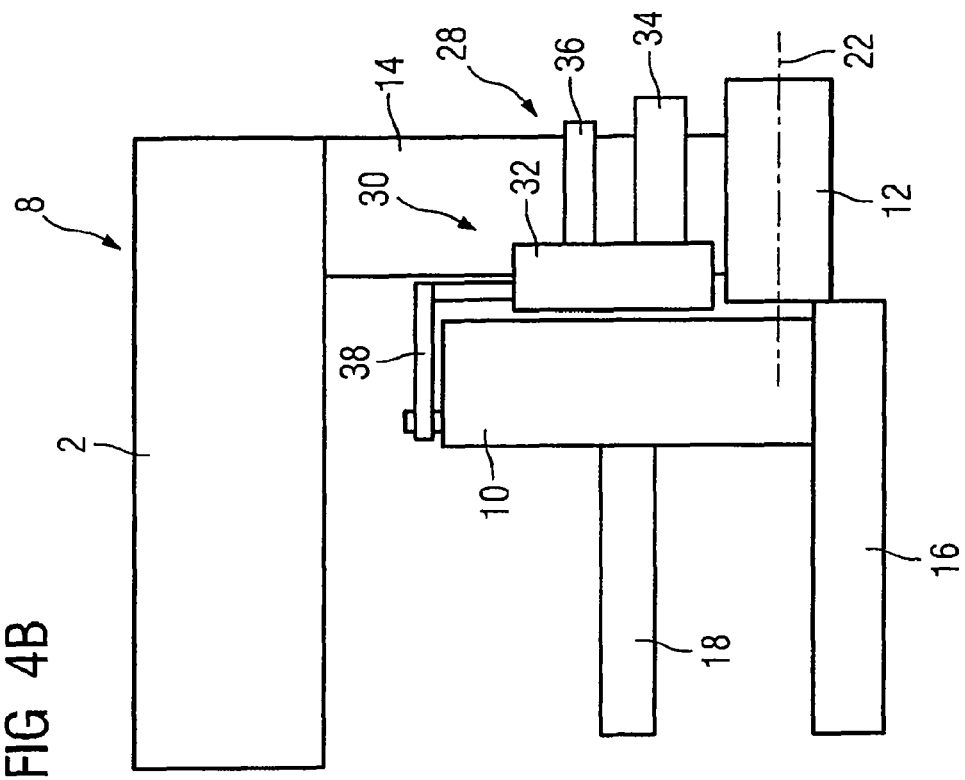
FIG. 4A illustrates a side view of an appliance rack with a biopsy unit in a biopsy position.
Figure 4B:
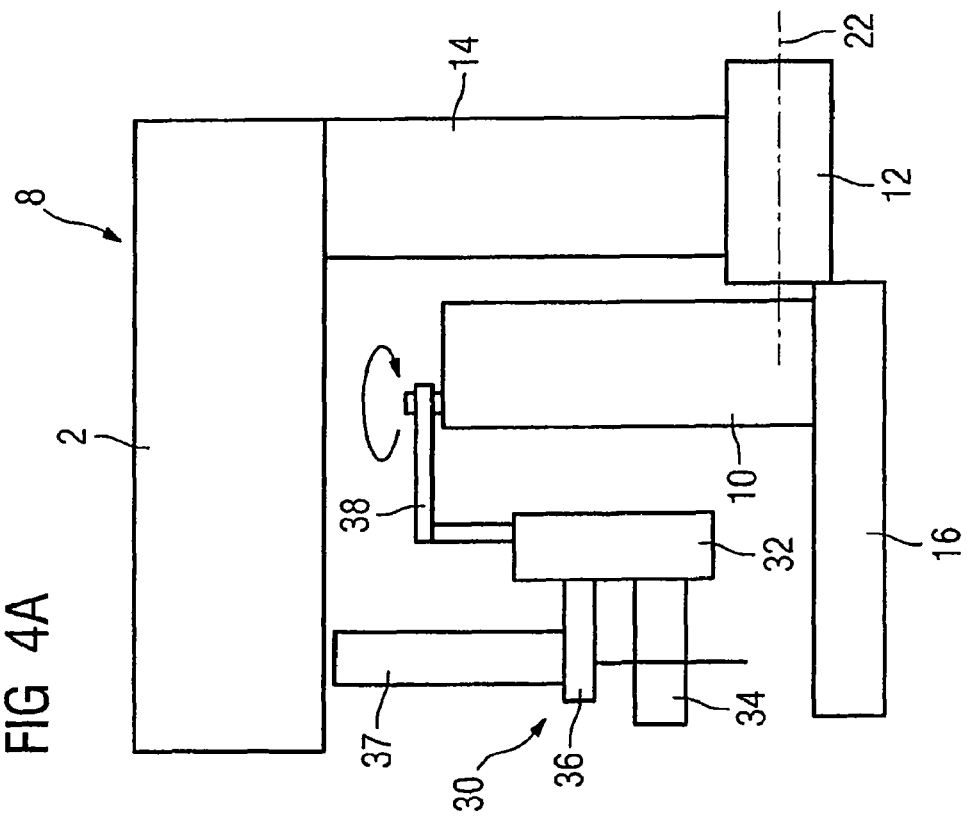
FIG. 4B illustrates a side view of the appliance rack according to FIG. 4A, wherein the biopsy unit is arranged in a parked position.

An appliance rack 8 with an integrated biopsy unit 30 can be seen in FIGS. 4A, 4B. The biopsy unit 30 includes a biopsy support column 32 to which a holder 36 for a punch biopsy appliance 37 is fixed. A biopsy compression plate 34 is provided which can be moved toward the object table 16.

If a biopsy is to be performed, the biopsy unit 30 is swiveled into the operational or biopsy position provided in FIG. 4A. The breast to be treated is hereby fixed between the object table 16 and the biopsy compression plate 34. The biopsy is performed in that a biopsy needle is introduced and tissue samples taken. X-ray images can be produced before and after the biopsy and optionally concomitantly with the biopsy.

After the end of the biopsy, the biopsy unit 30 is moved into its parked position and placed in the parking space 28. In the exemplary embodiment according to FIGS. 4A and 4B, only one swivel movement is required to move the biopsy unit 30 from the parked position into the biopsy position. For this, the biopsy unit 30 is attached to a swivel arm 38, which is arranged swivelably on the compression unit 10.

Figure 5A:
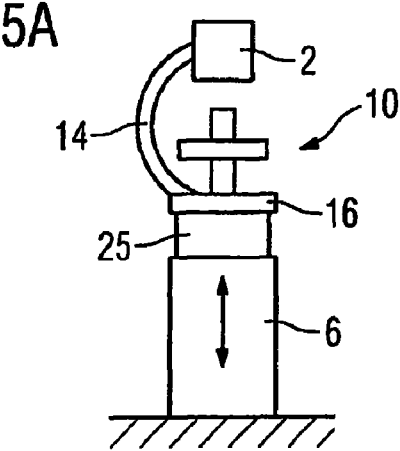
FIG. 5A illustrates a mammography appliance with a height-adjustable stand.
Figure 5B:
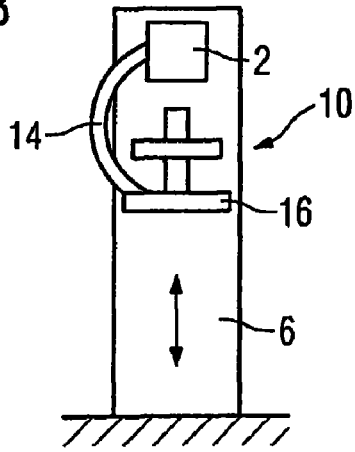
FIG. 5B illustrates a mammography appliance, in which an appliance rack is vertically adjustable relative to the stand
Figure 5C:
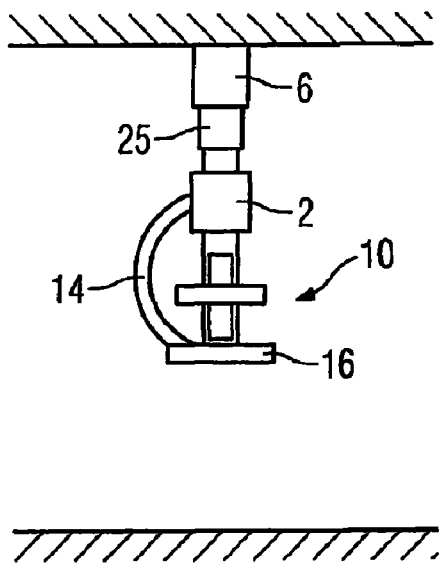
FIG. 5C illustrates a mammography appliance, in which the stand is attached at the ceiling side

FIGS. 5A-5C show different variants of the mammography appliance. With the embodiment according to FIG. 5A, the stand is vertically adjustable and the appliance rack 8 is connected by the bearing element 12 to the stand 6 and arranged above the stand 6.

With the variant according to FIG. 5B, the appliance rack 8 is arranged directly in front of the front side of the stand 6. The appliance rack 8 is vertically adjustable relative to the stand 6. The two variants in FIGS. 5A, 5B are provided for floor assembly. FIG. 5C now shows a variant for ceiling assembly in which the stand 6 embodied as a lifting system is attached to the ceiling. With this variant, once again the irradiation unit 2 is arranged above the object table 16. Here, the stand 6 extends as far as the lower region of the C-arm 14, on which the bearing element 12 (not shown in any more detail here) is provided in order to facilitate the swiveling movement.

While the invention has been described above by reference to various embodiments, it should be understood that many changes and modifications can be made without departing from the scope of the invention. It is therefore intended that the foregoing detailed description be regarded as illustrative rather than limiting, and that it be understood that it is the following claims, including all equivalents, that are intended to define the spirit and scope of this invention.

The invention claimed is:

1. A mammography appliance comprising:
an appliance rack comprising an irradiation unit, an object table, and a compression unit; and
a stand attached to the appliance rack,
wherein the irradiation unit is attached to a C-arm support arm the C-arm support arm lying in a swivel plane that is perpendicular to a horizontal axis, and
wherein an end of the C-arm support arm is telescopic, and the irradiation unit is arranged on the telescopic end of the C-arm support arm.

2. The mammography appliance as claimed in claim 1, wherein the C-arm support arm is pivotably mounted about the horizontal axis.

3. The mammography appliance as claimed claim 1, wherein the C-arm support arm is arranged directly in front of the stand in the swivel plane.

4. The mammography appliance as claimed in claim 1, wherein the stand includes a bearing element on which the C-arm support arm is attached rotatably about the horizontal axis.

5. The mammography appliance as claimed in claim 3, wherein the appliance rack is attached to the bearing element at the face end on the stand.

6. The mammography appliance as claimed in claim 4, wherein the C-arm support arm is mounted with an end-side mounting end on the bearing element.

7. The mammography appliance as claimed in claim 6, wherein the compression unit is operable to be rotated together with the C-arm support arm on the bearing element about the horizontal axis.

8. The mammography appliance as claimed in claim 1, wherein the appliance rack comprises a biopsy unit which is operable to be moved from a parked position into a biopsy position.

9. The mammography appliance as claimed in claim 8, wherein the parked position is arranged in a free parking area encompassed by the C-arm-support arm.

10. The mammography appliance as claimed in claim 8, wherein the biopsy unit is pivotably mounted on the compression unit.

11. The mammography appliance as claimed in claim 1, wherein the stand includes a display, an operator panel or a display and an operator panel, which viewed in a horizontal projection, is arranged in a free space between the compression unit and the irradiation unit.

12. The mammography appliance as claimed in claim 1, wherein the stand is vertically adjustable with the appliance rack.

13. The mammography appliance as claimed in claim 1, wherein the appliance rack is vertically adjustable relative to the stand.

14. The mammography appliance as claimed claim 1, wherein the C-arm support arm is arranged in a longitudinal direction of the stand in the swivel plane.

15. The mammography appliance as claimed in claim 3, wherein the appliance rack is attached to the bearing element at the face end on the stand.

16. The mammography appliance as claimed in claim 5, wherein the C-arm support arm is mounted with an end-side mounting end on the bearing element.

17. The mammography appliance as claimed in claim 16, wherein the compression unit is operable to be rotated with the C-arm support arm on the bearing element about the horizontal axis.

18. The mammography appliance as claimed in claim 9, wherein the biopsy unit is pivotably mounted on the compression unit.

* * * * *